US009655563B2

(12) United States Patent
Liu et al.

(10) Patent No.: US 9,655,563 B2
(45) Date of Patent: May 23, 2017

(54) EARLY THERAPY RESPONSE ASSESSMENT OF LESIONS

(71) Applicant: SIEMENS HEALTHCARE GMBH, Erlangen (DE)

(72) Inventors: David Liu, Franklin Park, NJ (US);
Shaohua Kevin Zhou, Plainsboro, NJ (US); Martin Kramer, Erlangen (DE);
Michael Sühling, Erlangen (DE);
Christian Tietjen, Furth (DE);
Grzegorz Soza, Heroldsberg (DE);
Andreas Wimmer, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 317 days.

(21) Appl. No.: 14/471,501

(22) Filed: Aug. 28, 2014

(65) Prior Publication Data
US 2015/0087957 A1  Mar. 26, 2015

Related U.S. Application Data

(60) Provisional application No. 61/882,143, filed on Sep. 25, 2013.

(51) Int. Cl.
*A61B 5/05* (2006.01)
*A61B 5/00* (2006.01)
(Continued)

(52) U.S. Cl.
CPC .......... *A61B 5/7267* (2013.01); *A61B 5/7264* (2013.01); *A61B 6/032* (2013.01);
(Continued)

(58) Field of Classification Search
CPC ..... A61B 5/7267; A61B 5/7264; A61B 6/032; A61B 6/5229; A61B 6/5217; A61B 5/4244; A61B 5/055; A61B 2576/00; A61B 5/7275; A61B 5/742; A61B 5/4848; G06T 7/42; G06T 7/0016; G06T 2207/30096; G06T 2207/10136; G06T 2207/20016;
(Continued)

(56) References Cited

U.S. PATENT DOCUMENTS

2004/0236225 A1\* 11/2004 Murphy ................ A61B 5/015
600/473
2005/0041843 A1\* 2/2005 Sawyer ................ A61N 5/1049
382/128

(Continued)

OTHER PUBLICATIONS

PCT International Search Report mailed Jan. 15, 2015 corresponding to PCT International Application No. PCT/US2014/057175 filed Sep. 24, 2014 (14 pages).

(Continued)

*Primary Examiner* — Sanjay Cattungal

(57) ABSTRACT

For therapy response assessment, texture features are input for machine learning a classifier and for using a machine learnt classifier. Rather than or in addition to using formula-based texture features, data driven texture features are derived from training images. Such data driven texture features are independent analysis features, such as features from independent subspace analysis. The texture features may be used to predict the outcome of therapy based on a few number of or even one scan of the patient.

13 Claims, 4 Drawing Sheets

(51) Int. Cl.
  *A61B 6/03* (2006.01)
  *A61B 6/00* (2006.01)
  *G06K 9/62* (2006.01)
  *G06T 7/00* (2017.01)
  *G06T 7/42* (2017.01)
  *A61B 5/055* (2006.01)

(52) U.S. Cl.
  CPC .......... *A61B 6/5217* (2013.01); *A61B 6/5229* (2013.01); *G06K 9/624* (2013.01); *G06K 9/6214* (2013.01); *G06K 9/6256* (2013.01); *G06K 9/6259* (2013.01); *G06T 7/0016* (2013.01); *G06T 7/42* (2017.01); *A61B 5/055* (2013.01); *A61B 5/4244* (2013.01); *A61B 5/4848* (2013.01); *A61B 5/7275* (2013.01); *A61B 5/742* (2013.01); *A61B 2576/00* (2013.01); *G06T 2207/10072* (2013.01); *G06T 2207/10136* (2013.01); *G06T 2207/20012* (2013.01); *G06T 2207/20016* (2013.01); *G06T 2207/20064* (2013.01); *G06T 2207/20081* (2013.01); *G06T 2207/20084* (2013.01); *G06T 2207/20104* (2013.01); *G06T 2207/30056* (2013.01); *G06T 2207/30096* (2013.01)

(58) Field of Classification Search
  CPC . G06T 2207/20064; G06T 2207/20081; G06T 2207/10072; G06T 2207/20084; G06T 2207/20104; G06T 2207/20012; G06T 2207/30056; G06K 9/6259; G06K 9/6214; G06K 9/624; G06K 9/6256

USPC ........................... 600/407–480; 382/128–132
See application file for complete search history.

(56) References Cited

U.S. PATENT DOCUMENTS

| | | | |
|---|---|---|---|
| 2013/0272593 | A1* | 10/2013 | Lee ........................ A61N 5/103 382/131 |
| 2013/0329973 | A1* | 12/2013 | Cao ...................... A61B 5/0033 382/128 |
| 2015/0282714 | A1* | 10/2015 | Mueller ................. H04N 5/225 348/37 |

OTHER PUBLICATIONS

Peter Maday et al: "Imaging as a Surrogate for the Early Prediction and Assessment of Treatment Response through the Analysis of 4-D Texture Ensembles (ISEPARATE)", Sep. 20, 2010, Medical Computer Vision. Recognition Techniques and Applications in Medical Imaging Springer Berlin Heidelberg, Berlin, Heidelberg, pp. 164-173, XP019160105.

A. Hyvärinen, et al., "Natural Image Statistics," A probabilistic approach to early computational vision, pp. 1-487, 2009.

R. Haralick, et al., "Texture features for image classification," IEEE Trans Sys Man Cyb. 3, pp. 610-621, 1973.

L. K. Soh, et al., "Texture analysis of SAR sea ice imagery using gray level co-occurrence matrices," IEEE Trans Geosci Remote Sens. 37(2), pp. 780-795, 1999.

* cited by examiner

EARLY THERAPY RESPONSE ASSESSMENT OF LESIONS

RELATED APPLICATION

The present patent document claims the benefit of the filing date under 35 U.S.C. §119(e) of Provisional U.S. Patent Application Ser. No. 61/882,143, filed Sep. 25, 2013, the disclosure of which is hereby incorporated by reference.

BACKGROUND

The present embodiments relate to early therapy response assessment. In particular, computer-aided response assessment is provided.

The response of a tumor under therapy is measured based on geometric measures, such as the diameter (e.g., RECIST or WHO criteria) or volume. A clinician monitors the geometric measures in radiological scans (e.g. CT or MRI) for a long period of time until a decision can be made about outcome. Many rounds of therapy are performed before the clinician makes a decision based on the geometric measures about whether the therapy is likely to succeed or not. Long periods of therapy may result in higher dosage for the patient (e.g., radiation therapy and/or x-ray imaging for the geometric measures) and greater cost of the therapy drugs.

Typically, the lesion appearance (e.g. enhancement pattern) changes earlier than geometric changes of the lesion occur. The lesion may maintain its size for a longer time while its tissue is already turning necrotic. The texture of a lesion gives insight into the therapy response at a much earlier stage, when the size or shape of the lesion is still largely unaffected. Using texture as a parameter, it may be possible to identify cases with a similar medical condition in a database for which the applied therapy and its outcome are known. This may help the doctor in estimating the effectiveness of different therapies and chose the best strategy. However, such approaches are time consuming and/or difficult for a doctor or other person to perform.

SUMMARY

Systems, methods, and computer readable media are provided for therapy response assessment. Texture features are input for machine learning a classifier and for using a machine learnt classifier. Rather than or in addition to using formula-based texture features, data driven texture features are derived from training images. Such data driven texture features are independent analysis features, such as features from independent subspace analysis. The texture features may be used to predict the outcome of therapy based on a few number of or even one scan of the patient.

In a first aspect, a method is provided for therapy response assessment. Pre-therapy and post therapy medical images of a patient are obtained. The medical images represent at least one lesion of the patient. A processor convolves the pre-therapy and post therapy medical images with a texture feature learned from training images. The processor classifies a therapy response of the lesion with a machine-learnt classifier with a result of the convolving as an input feature to the machine-learnt classifier.

In a second aspect, a non-transitory computer readable storage medium has stored therein data representing instructions executable by a programmed processor for therapy response assessment. The storage medium includes instructions for: with only one or two scans, extracting texture features for a lesion with a filter kernel, the filter kernel being independently based on image data; and predicting an outcome of therapy on the lesion, the predicting being a function of the texture features.

In a third aspect, a method is provided for therapy response assessment. A processor subjects patches of lesions represented in a plurality of training frames of data to independent subspace analysis. The processor creates a number of image filters from the independent subspace analysis of the patches and calculates texture features by application of the image filters to the lesions as represented in the training frames of data. The processor learns a predictor of therapy response as a function of the texture features.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

In therapy response assessment, a computer assists a doctor in estimating the effectiveness of different cancer therapies and choosing the best strategy. Given the variability of lesions, imaging settings, situations, and number of cases, it may take a doctor or other medical professional an unreasonable amount of time to identify similar cases and patients for making an informed prediction. As a result, there may be a great amount of variability in predictions by different medical professionals. A computer may more quickly access the information and more consistently predict therapy response. Given the subtlety of prediction from, at least in part, medical images, a processor may better perform or at least provide a more efficient second perspective on therapy response assessment.

In order to judge the state of a tumor or lesion in an objective manner, measures of therapy response suitable at early therapy stages are used. The effect of the therapy is assessed as early as possible. Using two scans, or possibly with only one scan, the predictor may decide whether the therapy will fail or succeed. Queues that may be missed by a doctor with such a few images may be identified by the processor applying the predictor. The decision making happens at an earlier stage.

Figure 1:
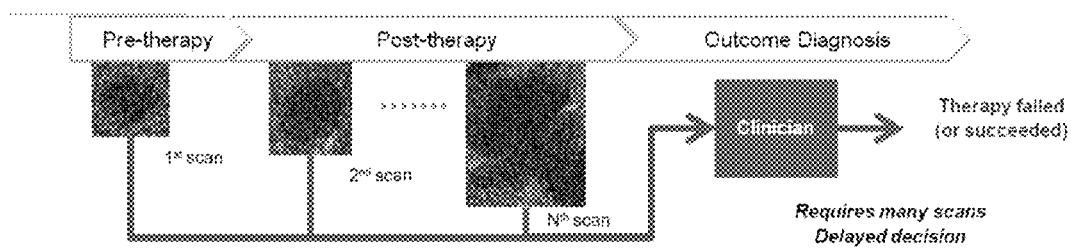
FIG. 1 shows an example process for therapy response assessment using geometric measures.
Figure 2:
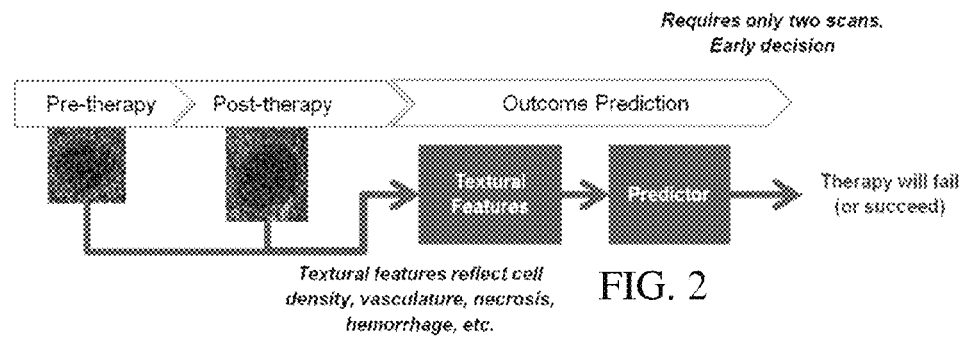
FIG. 2 shows an example process for therapy response assessment using texture features.

FIG. 1 shows an approach using geometric measures where a pre-therapy scan is performed and then a sequence of N (e.g., 5 or more) scans are performed after therapy or during a sequence of therapy applications. The clinician then uses the scans to determine geometric changes to predict the success or failure of the therapy. Meanwhile, the patient has been exposed to the medications and/or radiation associated with therapy and/or monitoring many times. Conversely, FIG. 2 shows acquiring the pre-therapy scan and a single post therapy scan. Texture features reflecting cell density, vasculature, necrosis, hemorrhage, other characteristics, or combinations thereof are extracted and used for automated (e.g., machine learnt) prediction of success or failure of the therapy. The prediction may be made earlier in the process, possibly avoiding further therapy where the outcome is likely negative. The prediction may be made based on the pre-therapy scan before therapy. Early therapy outcome prediction is provided, possibly reducing exposure of a patient to therapy that is likely not successful.

In the prediction, the texture of organs and/or lesions is used to predict the likelihood of future cancer development. The features are extracted using Independent Subspace Analysis (ISA) or other data-driven approach. Rather than or in addition to using programmer designed formulas for measuring texture, training scans are used to determine texture that is appropriate for and/or determinative of outcome for a given type of lesion, organ, therapy, and/or other situation. This is different from traditional features where a fixed formula describes how to calculate the feature value. With ISA or other data-driven development of the texture features, different sets of training images and ground truth labels may generate different image filters, and hence different feature values. The advantage of such a data-driven approach is that, as the training dataset grows larger, more meaningful patterns of texture may be discovered without relying on expert knowledge to manually define heuristic and sub-optimal mathematical formulas for patterns. The learning-based approach also allows training the system for different therapy types (e.g. chemo-therapy, targeted therapy, radiation therapy) resulting in therapy-specific response features that are automatically learnt. Data-driven texture features allow for different features to be learned for different types of lesions, tissues, therapy, and/or imaging modalities.

Figure 3:
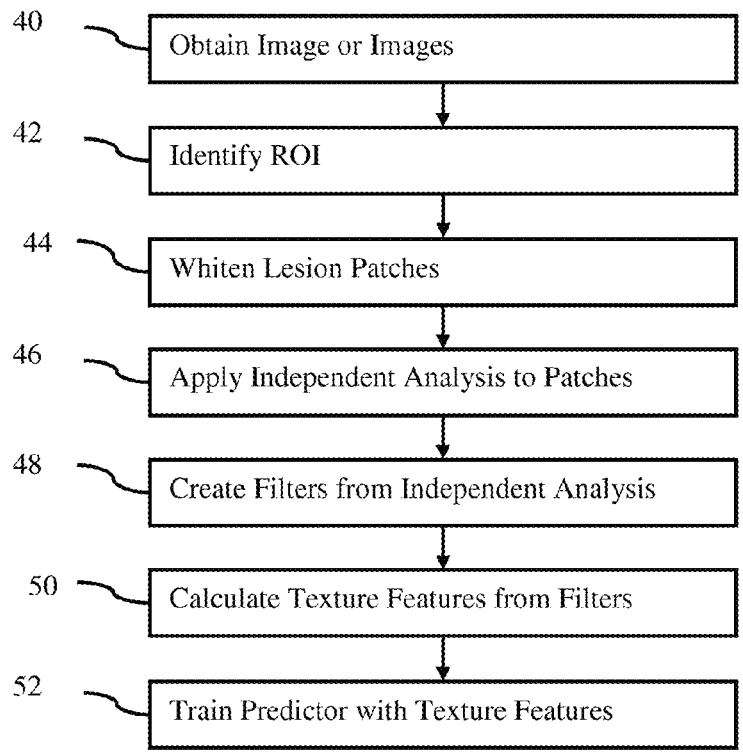
FIG. 3 is a flow chart diagram of one embodiment of a method for training in therapy response assessment.
Figure 6:
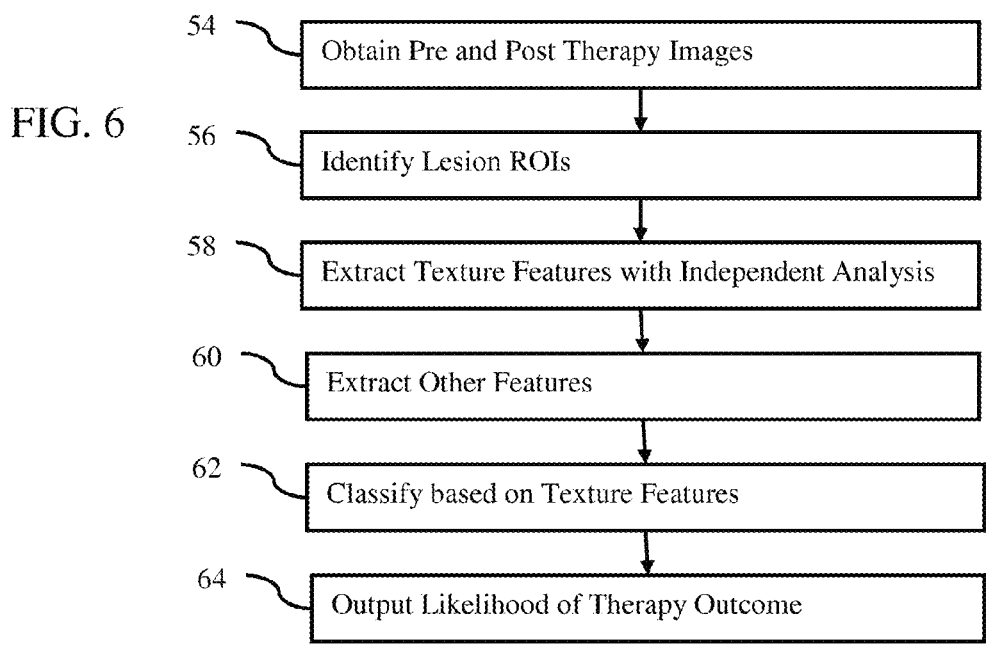
FIG. 6 is a flow chart diagram of one embodiment of a method for application in therapy response assessment.

FIGS. 3 and 6 show methods for therapy response assessment. The method for therapy response assessment may be a method to learn how to access outcome of therapy or may be a method for assessing the outcome with a learnt predictor. FIG. 3 is directed to machine training of the therapy outcome predictor. FIG. 6 is directed to application of a machine-learnt therapy outcome predictor. In both cases, a machine, such as a processor, computer, or server, implements some or all of the acts. The system of FIG. 7 implements the methods in one embodiment. A user may select the image files for application of the therapy response predictor by the processor, select the image from which to learn features by a processor, and/or identify a region of interest. Use of the machine allows processing large volumes (e.g., images of many pixels and/or many images) of information that may not be efficiently handled by humans (at least in comparative time frames for a given volume of information), may be unrealistically handled by humans in the needed time frame, or may not even be possible by humans due to subtleties and/or timing.

The methods are provided in the orders shown, but other orders may be provided. For example in FIG. 6, acts 58 and 60 may be performed in parallel or opposite order.

Additional, different or fewer acts may be provided. For example, act 44 of FIG. 3 is not provided. As another example, acts 60 and/or 64 of FIG. 6 are not provided. In yet other examples, acts for capturing images and/or acts using detected information are provided. Acts for configuring, input, or output may be provided.

FIG. 3 shows a method for learning in therapy response assessment. A processor performs the learning, such as by performing acts 44-52. The processor both creates texture features from training data in acts 46-48 and learns a predictor with the texture features as inputs in act 52. The learnt feature may be used by the processor to calculate a feature value and/or by the processor to train a classifier.

In act 40, one or more images of an object are obtained. The images are obtained by data transfer, capture, and/or loading from memory.

The images are frames of data representing a patient at given times. The images are scalar values or display values (e.g., red green blue (RGB)). The images may have been previously displayed or have not yet been displayed.

The images are acquired from a scan. The images are captured using any one or more sensors. For example, images of organs are captured using x-ray, computed tomography (CT), fluoroscopy, angiography, magnetic resonance, ultrasound, positron emission tomography, or single photon emission computed tomography. A given pre or post therapy scan provides one or more images. For example, images for different phases of a multiple phase contrast enhanced scan (e.g., native, arterial, and venous phases of contrast agent wash in and/or wash out) are acquired. As another example, Dual Energy CT images, including an iodine map, are acquired as part of a scan.

The pre and post therapy scans are the same or different types of scans. Each scan provides one or multiple images. Multiple images of the same or different patients use the same or different imaging modality with the same or different settings (e.g., field of view).

The object of interest in a medical image may be an organ, a cyst, a tumor, calcification or other anomaly. Any type of lesion may be imaged. The organ surrounding the lesion may be scanned. The image may represent healthy tissue. The image may represent the lesion in two or three-dimensions. For example, the image may be of pixels or voxels.

For training, images are acquired for the same type of lesion with or without other common arrangements (e.g., patient characteristics (male vs. female or age), imaging modality, organ, type of therapy, and/or stage). Pre and post therapy images for many, such as tens, hundreds, thousands, or more, patients are obtained. The images are associated with or linked to known outcomes. For example, all of the images are labeled with ground truth. For creating texture features, just the images associated with positive outcome are used. Alternatively, just images associated with negative outcome or both positive and negative outcomes are used. For training the predictor, images labeled for both positive and negative outcome are used.

In act 42, one or more regions of interest (ROI) are identified in each of the images. Manual (e.g., user input) or automated tumor detection or segmentation is used to find the region of interest. Any now known or later developed region of interest identification may be used.

The region of interest is a bounding box or other shape enclosing the lesion or is a segmentation specifically of the lesion. More than one region of interest may be provided on a given image. For example, multiple lesions are represented in a given image. As another example, one or more regions of interest for healthy tissue are identified. In one embodiment, nested regions of interest are provided, such as one for an organ as a whole or in part and a sub-set of that region being a region for a lesion.

The region of interest is to be used for feature extraction. Tumor associated features may be extracted from within the region of interest. The approach is to combine multiple sets of different features for training a classifier. Such features may also be extracted from other reference regions in the image data, such as the whole liver parenchyma, to complement the tumor features extracted from within the lesion specific ROI and to provide the classifier with additional information.

The delineated lesion region of interest may be expanded to assure that the border or gradient from lesion to healthy tissue is included. The region of interest is dilated (enlarged) by the processor to include surrounding information. The dilation is by a percentage (e.g., 5-10% expansion), by a number of samples (e.g., adding 2-10 samples from a center), or by another process. Alternatively or additionally, the region of interest is originally defined by the user or processor to include the surrounding information. In alternative embodiments, no expansion is provided.

The region of interest may be sub-divided. For example, a moving window is defined to cover a part of the region of interest. By moving the window with any step size (e.g., 1 pixel, 2 pixels, or other distance), overlapping sub-sets of the region of interest are defined. These patches or sub-sets are uniformly defined within the region of interest with a fixed step size. Any size of patch may be used, such as 8×8 pixels. In alternative embodiments, the patch size and/or step size vary or are not uniform.

In act 44, the patches are whitened by the processor. Within each kernel or patch, the values are altered to set the mean to a zero value and make the variance equal to one. Other normalization may be used. In one embodiment, the patches are whitened with a principal component analysis. Alternatively, whitening is not performed.

In act 46, independent subspace analysis (ISA) or independent component analysis (ICA) is applied to the patches, such as the whitened patches. The independent analysis examines the data of the patches to find text patterns. The processor analyzes many or all of the patches of many or all of the regions of interests from the different patients to learn one or more texture features. Data-driven machine learning is used by the processor to recognize one or more patterns common across various patches and patients. Both ISA and ICA find features that form independent subspaces, but ISA is found to be more robust to local variations than ICA.

In one embodiment, the patches are subjected to independent subspace analysis (ISA) by the processor. In another embodiment, the patches are subjected to independent component analysis by the processor. The patches are decomposed into different components to find patterns. Other pattern recognition, with or without independence, may be used.

The independent analysis or other pattern recognition by the processor from the many examples results in a number, N, of image filters. In act 48, the image filters are created by the application of the independent analysis in act 46. Any number of common patterns in the various training examples may be created. For example, five image filters are learned from the training images.

To distinguish texture of lesions with desired response from others, the ground truth is used. The training data associated with desired outcome, as indicated by the ground truth, is used for creating the image filters. Alternatively or additionally, other training data is used. In other embodiments, the independent analysis learns texture features that distinguish between texture with desired outcome from texture with an undesired outcome, so the training data is divided into sets based on the ground truth. In alternative embodiments, the image filters are created without consideration of ground truth. Texture common to both necrotizing and non-necrotizing lesions are found by computer implemented analysis.

The image filters have a same size and shape as the patches. Alternatively, the image filters have a different size and/or shape as the patches. The image filters are binary masks or include any number of gradations, such as including an average or full dynamic range of the patches from the training data.

Figure 4:
FIG. 4 illustrates example texture features learned from training images.

FIG. 4 shows five example image filters learned by a processor from pattern recognition using independent subspace analysis. The image filters were created in act 48 from CT images of liver tumors of patients. These image filters represent more common patterns across the set of lesions for the training data. The same, different, or no image filters are created for healthy tissue. Given different training data, different image filters may result.

In act 50, texture features are calculated by the processor. The image filters (see FIG. 4 for example) represent texture features for a given situation, but are not themselves the inputs for learning a predictor. The image filters are applied to the training data to calculate values for the texture features. The image filters are applied to the same training data from which the image filters were created. Alternatively, a different set of training data is used.

The image filters are applied to the appropriate regions of interest. For image filters representing lesion texture, the image filters are applied to lesions as represented in the training data. For image filters representing healthy tissue or a combination of healthy tissue and lesion tissue, the image filters are applied to the regions of interest for that combination.

The image filters are applied by spatial filtering. The image filters are one, two, or three-dimensional filters. The N filters are applied to each tumor by a convolution operation (e.g., dot product or other similarity measure). The image filter is positioned relative to the legion and the intensities of the image filter are multiplied with the data of the image in the patch of the region of interest. A sum or average of the resulting multiplications provides a value for the image filter at that position. By shifting the image filter, such as was done for the patches, values for different locations are determined. Any convolution of the image filters with the lesions as represented in the training frames of data may be used.

Figure 5A:
FIGS. 5A-C show results of convolving the features of FIG. 4 with three different lesions.
Figure 5B:
Figure 5C:
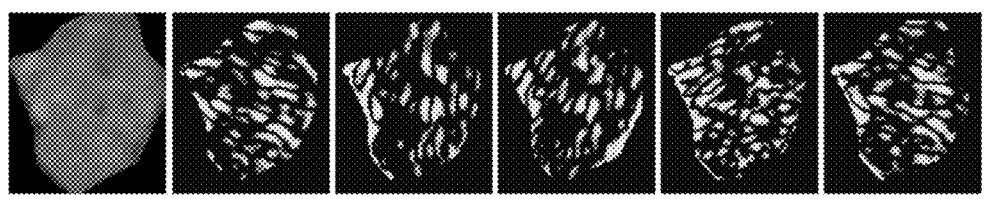

FIGS. 5A-C show convolution results of the image filters of FIG. 4 with three different lesions. The left to right sequence of texture features represented by the image filters of FIG. 4 is maintained in FIGS. 5A-C. The left most CT slice image is of the lesion being filtered. Where the lesion includes texture more closely resembling the image filter, the resulting pixel has a higher intensity (e.g., more white). The differences in scale between FIGS. 5A-C are due to differences in scale and/or size of the lesion.

The resulting values (i.e., filter responses) from the convolution are combined to indicate a feature value for that lesion based on the given image filter. For example, the intensity values are summed or averaged. In the example of FIG. 5A, the average intensity for each of the texture features is calculated, providing a single value for each image filter. For example, the average response per filter per tumor is recorded as a value of the ISA feature. Alternatively, a feature is calculated from the results of the convolution, such as using a Haar wavelet feature or other pre-designed feature from the data driven feature provided by the image filter convolution with the image data.

The resulting values are the texture features as used for the training in act 52. Other information may be used as part of the input feature vector for training. The other information may represent the patient (e.g., age, sex, or family history), stage of the lesion, type of therapy, other situational information, and/or other image derived features.

In one embodiment, other texture features are determined from the training data. For example, Haralick texture features, such as contrast, entropy, and/or others, are used. In another example or in addition, homogeneity, energy, and dissimilarity texture features are used. The homogeneity, for example, has the following equation:

$$HGT = \Sigma_{i=1}^{N_g} \Sigma_{j=1}^{N_g} P(i,j)/(1+|i-j|)$$

where P(i, j) counts the number of times a pixel with value i is adjacent to a pixel with value j and then dividing by the total number of such comparisons made. $N_g$ is the number of gray levels in the image. The texture features rely on predetermined formulas rather than features learned from training data by a processor. Any now known or later developed texture features may be used.

In another additional or alternative embodiment, texture features based on local binary patterns are used. The local binary patterns compare the intensity of each pixel with its neighboring pixels and return a code that compactly summarizes the differences. These codes are then summarized over the ROI through a histogram. A data pyramid may be used, where the same image at different resolutions (e.g., by decimation) is provided. The local binary patterns are then calculated for each resolution or level of the pyramid, as each pyramid level contains textural information in different scale and details.

In one embodiment, the texture features are calculated from the training data for one pre-therapy scan and one post therapy scan. In alternative embodiments, only pre-therapy scan, only the first post therapy scan, or additional post therapy scans are used.

The texture features, whether data driven or other texture features, are the same for pre and post therapy scans. In alternative embodiments, different features are provide for different scans relative to the therapy (i.e., learn texture features for pre-therapy images different than texture features learned from post therapy images).

Once the values for the input feature vector are calculated and/or obtained, the ground truth for therapy response is used to train, by a processor, the predictor of the therapy response. The ground truth is binary, such as successful or not successful outcome from therapy. Alternatively, the ground truth has a greater resolution, such as the number of months without re-occurrence, time of remission, change in size, time to narcotization, or other measure of success of therapy.

In act 52, a predictor of therapy response is learned by a processor. The processor uses the ground truth and data-driven texture features, with or without other features to train a classifier. Any machine learning may be used, such as a probabilistic boosting tree, support vector machine, or other machine learning classifier. Other classifiers may include a single class or binary classifier, collection of different classifiers, cascaded classifiers, hierarchal classifier, multi-class classifier, model-based classifier, or combinations thereof may be used. Multi-class classifiers include CART, K-nearest neighbors, neural network (e.g., multi-layer perceptron), mixture models, or others. Error-correcting output code (ECOC) may be used.

In one embodiment, the features are fed into a machine learning classifier or regressor, such as a Support Vector Machine (SVM) or Regression Random Forest, for training. The training provides a matrix associating input values of features to outputs or predictions. The matrix or trained classifier (e.g., learnt classifier) is a predictor of the therapy response. During training, the set of ground truth cases with known therapy outcome are provided for learning the system parameters. The predictor may be used predict the therapy outcome early in the therapy process, such as from one, two, or less than five scans.

Different predictors may be learnt using different training data. The system may be trained for different lesion entities (liver, lung, lymph nodes, or other), different therapies, different cohorts of patients, different imaging modality, or other differences, resulting in specific therapy response features that are automatically learnt. Either separate systems can be trained or the system may incorporate additional non-image features, such as the type of therapy, lesion entity, or time after onset of therapy to augment image-based features. Alternatively, a predictor generic to different situations (e.g., different types of lesions, different organs, or different imaging modality) is trained from training data with the same generic situation.

During the optimization to train the predictor, different distinguishing features are learned. Less than all of the input features may be determinative in a given situation. The training may select some features and not others to be used for predicting therapy response. The learning may indicate only a sub-set of features to be used for classification. In alternative embodiments, all of the features of the input feature vector are used by the learnt predictor.

The learnt predictor is applied to assess therapy response for a given patient. For patients with a same type of lesion or other situation, the same learnt predictor may be used. FIG. 6 shows one embodiment of application for therapy response assessment. The same or a different processor than used for training performs the acts of FIG. 6. For example, the matrix is used by a server for online assessment by customers. As another example, a medical institution purchases the matrix and applies the matrix for use with their patients.

In act 54, one or more images are obtained. The images are obtained by transfer, loading from memory, or as output by scanning. The images are pre and/or post therapy images for the patient. In one embodiment, the images are from a pre-therapy scan and only a few (e.g., only one or only two) post therapy scans. In yet other embodiments, an image or images from only one scan (e.g., pre or post therapy) are used.

The images represent a lesion in the patient. Multiple lesions may be represented. The data representing the lesion is obtained by medical imaging, such as from CT scanning with a CT system. An x-ray source and detector mounted on a gantry scan the patient. A computer reconstructs a volume of the patient from the detected x-ray attenuations. A slice or projection from the volume may be used as a frame of data of an image representing the lesion. Other computed tomography images may be used, such as contrast enhanced or iodine images.

In act 56, one or more regions of interest are identified. The lesion as represented in each of the images is located. The same or different segmentation or region designation used for training is used in application. For example, a processor automatically segments the legion from healthy tissue. As another example, a user manually positions a box designating the region of interest.

The region of interest includes the lesion and a border of the lesion. Surrounding information may or may not be included. The region may or may not be dilated to include the surrounding information.

In act 58, texture features are extracted with independent analysis. The independent analysis was performed for learning the texture features from the training data. The resulting texture feature is used in the application to extract one or more values. The image filters or filter kernels learned from the training data are convolved with the lesions as represented by the obtained images. The filter kernels are convolved with the regions of interest.

The convolution is performed for each of the images representing the lesion. The pre and/or post therapy medical images, at least for the regions of interest, are convolved with the filter kernels. Any number of filter kernels is used, such as three or more (e.g., five in the example of FIG. 4). Each filter kernel is convolved with each of the regions of interest in each of the images.

Since only one, only two, or a few number of scans are performed for early prediction, the texture features are extracted from this limited number of images. The filter kernels used to extract the texture features are learned from the images of many patients, but the resulting filter kernels are applied to the images of a given patient for application.

The texture feature (e.g., filter kernel) to be convolved with the image is learnt automatically from training images with or without ground truth information. The ground truth may be used to identify texture for desired outcome from texture with undesired outcome or therapy response. The texture feature for convolution with the images is based on independent analysis, such as independent subspace analysis. By using data to develop the texture feature, different texture features result from the use of different training data. Training data appropriate for a given application is used to provide the texture feature.

The convolution is limited to the appropriate regions of interest. For example, filter kernels developed for lesions are used to filter regions of interest corresponding to or representing lesions. The filtering is not performed outside of the region of interest.

The filter kernels are used to filter the images of the patient. The same or different calculation used to calculate feature value for training the classifier are used to calculate the value for the texture feature. For example, the results of the convolution are summed or averaged. The intensities output from the filtering are summed. The sum may be divided by the number of samples (e.g., pixels) in the region of interest.

In act 60, other features are obtained. Other texture features may be extracted. For example, filters defined by mathematical formulas are convolved with the images. Any formula-based texture features may be used, such as discussed above for training. Pre-designed texture features, such as Haar wavelets, homogeneity, or local binary patterns, may be calculated.

Other non-texture features may be calculated. The features may be geometric, such as change in area or volume. The features may be patient related, such as smoking history, medications, or family history. The features may be a stage or other score related to the lesion.

In act 62, a therapy response of the lesion of the patient is classified. A processor, implementing a machine-learnt classifier, predicts the therapy response. The features, such as one or more features resulting from convolving the data-driven or training data-based texture feature, are input to the predictor. The predicted response to therapy based on the input feature vector is output. The outcome of therapy is predicted as a function of the texture features.

In one embodiment, the prediction is performed without any geometric measures as input. In other embodiments, an area or volume may be included in the feature vector, but shrinkage or change over time of geometry is not included. Instead, texture information is used. In other embodiments, shrinkage or other change in geometry over time is used as an input feature with texture features.

In one embodiment, the therapy response is classified with just imaging features from data-driven or training data learnt texture features. In other embodiments, other imaging features are used, such as texture features from pre-designed or mathematical formula-based texture features in the classifier input feature vector.

For features from imaging, only features from the pre-therapy medical images and a limited number of post therapy medical images are used. The limited number of post therapy medical images corresponds to only one scan, only two scans, or only three scans. This provides for early assessment of therapy response. Additional images from other scans may be used in alternative embodiments. In an alternative embodiment, only one image, or images from only one scan are used, such as predicting therapy response from pre-therapy images or from a single post therapy scan.

The classification is performed with any machine-learnt classifier. For example, the predictor is a support vector machine or a regression random forest. Other classifiers may be used.

The classifier predicts an outcome of a given therapy. The prediction may occur after one round of therapy, so the classifier predicts an outcome of continuing therapy. After obtaining a post therapy scan and corresponding medical image or images, the success or not of the therapy sequence is predicted before progressing further in the therapy sequence. Alternatively, the outcome is predicted after therapy is complete, but before the lesion fully responds to the therapy.

The classifier outputs a likelihood of therapy success or failure for the lesion of the patient. The likelihood is a binary indication, such as success or failure (e.g., lesion eradicated or not, or lesion growth stopped or not). Alternatively, the likelihood is a success rating with a scale of three or more. For example, the likelihood is a percentage chance of success or failure of treatment. A SVM, Regression Random Forest, Bayesian, or other machine-learnt classifier may provide a probability as an output. The probability is a ranking or percentage likelihood of success or failure in treatment of the lesion.

The classifier may be trained based on any definition of success or failure. For example, stopping growth, causing a percentage shrinkage, eradicating, or causing necrosis may be used as the definition of success.

In act 64, the likelihood of therapy response is output. The output is to a display, to a computer, or to storage. For example, the likelihood is added to a computerized medical record for the patient. As another example, an image or multiple images of the lesion are displayed to the user. The likelihood is indicated on or adjacent to the image. Color coding, text, or a numerical value may be used to represent the likelihood.

Figure 7:
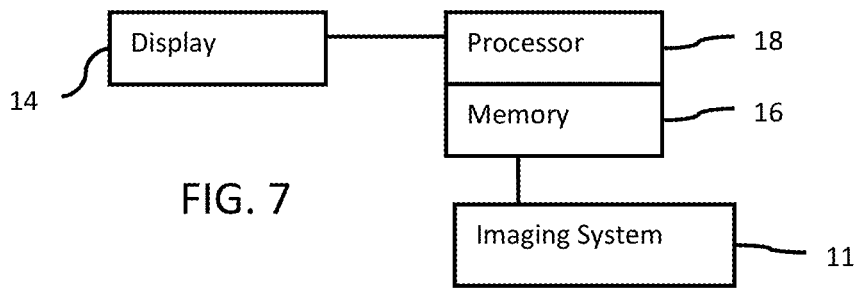
FIG. 7 is a block diagram of one embodiment of a system for therapy response assessment.

FIG. 7 shows a system for therapy response assessment. The system is a host computer, control station, work station, server, or other arrangement. The system includes the display 14, memory 16, and processor 18. Additional, different, or fewer components may be provided. The system is for training, such as using images from the medical imaging system 11 as ground truth. Alternatively, the system is for application of the learned features and classifier, such as using images from the medical imaging system 11 for predicting response to therapy for a patient. In other embodiments, the medical imaging system 11 is part of the system. In yet other embodiments, a picture archiving and communications system (PACS) or other memory is provided instead of or in addition to the medical imaging system 11 for supplying images.

The display 14, processor 18, and memory 16 may be part of a computer, server, or other system for image processing images from the medical imaging system 11. A workstation or control station for the medical imaging system 11 may be used. Alternatively, a separate or remote device not part of the medical imaging system 11 is used. Instead, the therapy assessment is performed remotely from the medical imaging system 11.

In one embodiment, the processor 18 and memory 16 are part of a server hosting the therapy response assessment function for use by a medical professional computer as the client. The client and server are interconnected by a network, such as an intranet or the Internet. The client may be a computer of the medical imaging system 11 or a computer of a medical professional, and the server may be provided by a manufacturer, provider, host, or creator of the therapy response assessment system.

The medical imaging system 11 is any now known or later developed imaging system. For example, the medical imaging system 11 is a computed tomography, ultrasound, x-ray, magnetic resonance, or functional imaging system. As a computed tomography system, an x-ray source and detector are mounted on or in a gantry on opposite sides of a patient space and corresponding patient bed. As the gantry moves the source and detector around the patient, a sequence of x-ray projections of the patient are acquired. A processor, such as the processor 18 or a different processor, reconstructs the x-ray attenuation in three-dimensions or for one or more slices.

The display 14 is a CRT, LCD, projector, plasma, printer, smart phone or other now known or later developed display device for displaying the images, learned texture features, and/or therapy response assessment information. For example, the display 14 displays two images, information about the images, therapy information, and an indication of whether the therapy is predicted to be successful. In a training environment, the display 14 may be of data-driven features, statistics, feature information, optimization information, or other training information.

The texture features (e.g., data learnt texture features), other features, classifiers, matrices, outputs, images, regions of interest, patches, and/or other information are stored in a non-transitory computer readable memory, such as the memory 16. The memory 16 is an external storage device, RAM, ROM, database, and/or a local memory (e.g., solid state drive or hard drive). The same or different non-transitory computer readable media may be used for instructions and other data. The memory 16 may be implemented using a database management system (DBMS) managed by the processor 18 and residing on a memory, such as a hard disk, RAM, or removable media. Alternatively, the memory 16 is internal to the processor 18 (e.g. cache).

The instructions for implementing the therapy response assessment in training or application processes, methods and/or techniques discussed herein are provided on non-transitory computer-readable storage media or memories, such as a cache, buffer, RAM, removable media, hard drive or other computer readable storage media (e.g., the memory 16). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

A program may be uploaded to, and executed by, the processor 18 comprising any suitable architecture. Likewise, processing strategies may include multiprocessing, multitasking, parallel processing and the like. The processor 18 is implemented on a computer platform having hardware, such as one or more central processing units (CPU), a random access memory (RAM), and input/output (I/O) interface(s). The computer platform also includes an operating system and microinstruction code. The various processes and functions described herein may be either part of the microinstruction code or part of the program (or combination thereof) which is executed via the operating system. Alternatively, the processor 18 is one or more processors in a network.

The processor 18 is configured to obtain images. A region of interest may be determined by the processor 18 or received from a user interface.

The processor 18 is configured to learn features or extract learned features. For example, an independent analysis is performed on a collection of regions of interest representing lesions. As another example, a learnt texture feature, such as a filter kernel from independent analysis, is applied by the processor 18. The processor 18 may train a classifier using the learned or data-driven features, training data, and ground truth information.

The processor 18 is configured to classify based on the learned features. The features are extracted from one or more images for a given patient. The values of the features are input to a learnt classifier. The processor 18 determines an output of the machine-learnt classifier based on the input features. The output is provided to the memory 16, the display 14, or a network interface.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for therapy response assessment, the method comprising:
    obtaining a pre-therapy medical image of a patient, the pre-therapy medical image representing at least one lesion of the patient;
    obtaining a post-therapy medical image of the patient, the post-therapy medical image of the patient representing the at least one lesion of the patient;
    convolving, by a processor, the pre-therapy and post therapy medical images with a texture feature learned from training images, the texture feature comprising an independent sub-space analysis feature; and
    classifying, by the processor, a therapy response of the lesion with a machine-learnt classifier with a result of the convolving as an input feature to the machine-learnt classifier.

2. The method of claim 1 wherein obtaining the pre-therapy and post therapy medical images comprises obtaining computed tomography images.

3. The method of claim 1 wherein obtaining the post-therapy medical image comprises obtaining only the post-therapy medical image or only the post-therapy medical image and one more post therapy medical image, and wherein classifying comprises classifying with the input feature including, for just features from imaging, only features from the pre-therapy and post-therapy medical images.

4. The method of claim 1 wherein convolving comprises convolving with the texture feature and at least two other texture features learned from the training images.

5. The method of claim 1 wherein convolving comprises convolving with the texture feature learned automatically from the training images and labeled ground truths.

6. The method of claim 1 wherein convolving comprises filtering with a kernel defined by the texture feature and summing intensities output from the filtering, the result being a function of the sum of the intensities.

7. The method of claim 1 wherein convolving comprises convolving with the texture feature comprising a training image-based feature such that different training images result in different texture features.

8. The method of claim 1 wherein classifying comprises classifying with a support vector machine or a regression random forest.

9. The method of claim 1 wherein classifying comprises predicting an outcome of continuing therapy after obtaining the post-therapy medical image.

10. The method of claim 1 wherein classifying comprises indicating a likelihood of therapy success or failure for the lesion.

11. The method of claim 1 further comprising identifying regions of interest in the pre-therapy and post-therapy medical images including the lesion and a border of the lesion, and wherein convolving comprises convolving the texture feature with the regions of interest and not with regions outside the regions of interest.

12. The method of claim 1 further comprising:
    convolving, by the processor, the pre-therapy and post therapy medical images with mathematical formula-based texture features;
    wherein classifying comprises classifying the therapy response with the result and results from the convolving with the mathematical formula-based textures features as an input vector including the input feature.

13. The method of claim 1 wherein convolving comprises spatially filtering the pre-therapy and post therapy medical images with a spatial kernel defined by the texture feature.

* * * * *